US011049031B2

(12) United States Patent
Chattopadhyay et al.

(10) Patent No.: US 11,049,031 B2
(45) Date of Patent: Jun. 29, 2021

(54) METHODS AND APPARATUS TO PREDICT SPORTS INJURIES

(71) Applicant: Intel Corporation, Santa Clara, CA (US)

(72) Inventors: Rita Chattopadhyay, Chandler, AZ (US); Kalpana A. Algotar, Chandler, AZ (US); Ali Ashrafi, Chapel Hill, NC (US); John Pilkin, Cary, NC (US)

(73) Assignee: Intel Corporation, Santa Clara, CA (US)

( * ) Notice: Subject to any disclaimer, the term of this patent is extended or adjusted under 35 U.S.C. 154(b) by 995 days.

(21) Appl. No.: 15/476,487

(22) Filed: Mar. 31, 2017

(65) Prior Publication Data

US 2018/0107936 A1 Apr. 19, 2018

Related U.S. Application Data

(60) Provisional application No. 62/409,707, filed on Oct. 18, 2016.

(51) Int. Cl.
*G06N 7/00* (2006.01)
*G16H 50/30* (2018.01)
(Continued)

(52) U.S. Cl.
CPC ......... *G06N 7/005* (2013.01); *A63B 24/0062* (2013.01); *G16H 20/30* (2018.01); *G16H 50/20* (2018.01); *G16H 50/30* (2018.01)

(58) Field of Classification Search
CPC ..... A63B 24/00; A63B 24/0062; A63B 69/00; A63B 57/00; G06N 7/00; G06N 7/005;
(Continued)

(56) References Cited

U.S. PATENT DOCUMENTS 8,352,488 B2   1/2013 Fleming et al.
8,447,420 B2   5/2013 Bloodworth
(Continued)

FOREIGN PATENT DOCUMENTS

WO   2015/021349   2/2015

OTHER PUBLICATIONS

Brockett, Camilla L., David L. Morgan, and U. W. E. Proske. "Predicting hamstring strain injury in elite athletes." Medicine & Science in Sports & Exercise 36.3 (2004): 379-387. (Year: 2004).*

(Continued)

*Primary Examiner* — Kamran Afshar
*Assistant Examiner* — Randall K. Baldwin
(74) *Attorney, Agent, or Firm* — Hanley, Flight & Zimmerman, LLC

(57) ABSTRACT

A disclosed example method to predict an injury for a target player on a target date includes determining a first probability of injury of the target player based on probabilities of injuries of second players having similarities with the target player; determining a second probability of injury of the target player based on injuries of the target player; determining a third probability of injury of the target player based on the first probability of injury of the target player and the second probability of injury of the target player; and generating, by executing an instruction with the processor, a report of a predicted probability of injury of the target player (Continued)

for the target date based on the third probability of injury of the target player.

22 Claims, 8 Drawing Sheets

(51) Int. Cl.
*G16H 50/20* (2018.01)
*G16H 20/30* (2018.01)
*A63B 24/00* (2006.01)

(58) Field of Classification Search
CPC ......... G06N 99/00; G06F 19/00; G06F 19/24; G06F 19/28; G06F 17/00; G06Q 10/06; G09B 9/00; A61B 8/00; A61B 5/00
See application file for complete search history.

(56) References Cited

U.S. PATENT DOCUMENTS

| | | | |
|---|---|---|---|
| 9,269,278 B1* | 2/2016 | Turner | G06F 19/3481 |
| 2002/0082806 A1* | 6/2002 | Kaub | G08G 1/164 |
| | | | 702/182 |
| 2004/0241629 A1 | 12/2004 | Ondrusz et al. | |
| 2006/0206027 A1* | 9/2006 | Malone | G06Q 50/22 |
| | | | 600/437 |
| 2012/0230555 A1 | 9/2012 | Miura et al. | |
| 2013/0331055 A1 | 12/2013 | McKown et al. | |
| 2015/0040685 A1* | 2/2015 | Nicholson | A61B 5/4064 |
| | | | 73/862.51 |
| 2016/0189007 A1 | 6/2016 | Wellington et al. | |
| 2016/0262694 A1 | 9/2016 | Calcano et al. | |
| 2016/0267663 A1 | 9/2016 | Sicking et al. | |
| 2016/0300347 A1* | 10/2016 | Dunn | G06T 7/60 |
| 2017/0161614 A1 | 6/2017 | Mehta et al. | |
| 2017/0220620 A1 | 8/2017 | Alzahrani | |
| 2017/0272842 A1* | 9/2017 | Touma | H04Q 9/00 |
| 2017/0281020 A1 | 10/2017 | Mulligan et al. | |

OTHER PUBLICATIONS

Leetun, Darin T., et al. "Core stability measures as risk factors for lower extremity injury in athletes." Medicine & Science in Sports & Exercise 36.6 (2004): 926-934. (Year: 2004).*
Brown, Matthew. The ability of the functional movement screen in predicting injury rates in division I female athletes. Diss. University of Toledo, 2011 (Year: 2011).*
Kampakis, Stylianos. "Predictive modelling of football injuries." arXiv preprint arXiv:1609.07480 (2016). (Year: 2016).*
International Searching Authority "International Search Report" issued in connection with PCT patent application No. PCT/US2017/044925 dated Nov. 9, 2017, 3 pages.
International Searching Authority "Written Opinion" issued in connection with PCT patent application No. PCT/US2017/044925, dated Nov. 9, 2017, 8 pages.
Loshin, "Spreading the Nexus of Intelligence: Blending Massive Connectivity with Cognitive Computing to Enable the Insightful Fog," Gigaom Research, Saffron Technology, Aug. 25, 2014, 17 pages.
Saffron Technology, "Natural Intelligence Platform: Fusing the Genius of the Brain with the Power of Computing," Oct. 2014, 10 pages.
Saffron Technology, "Your Brain is Cognitive, Not a Database: A Distributed Associative Memory Base for Natural Intelligence," Jun. 2014, 22 pages.
United States Patent and Trademark Office, "Non-Final Office Action," dated Feb. 5, 2020 in connection with U.S. Appl. No. 15/717,227, 12 pages.
United States Patent and Trademark Office, "Final Office Action," issued in connection with U.S. Appl. No. 15/717,227, dated Aug. 4, 2020, 18 pages.
United States Patent and Trademark Office, "Non-Final Office," issued in connection with U.S. Appl. No. 15/717,227, dated Nov. 19, 2020, 18 pages.

* cited by examiner

| Sr | Target Date | Target Day | Target Player ID | Target Player Name | Similar Player IDs | Similar Player Names | Similarity Matrix | # Of Games Played (Similar Players) | # Injuries (Similar Players) | Probability of Injury (Target Player) | # Ga (Tar |
|---|---|---|---|---|---|---|---|---|---|---|---|
| 961 | 2013-12-19 | Thursday | 10211 | Taj Gibson | 10533.1... | Iman Shu... | 0.7222.0... | 30,33,30... | 0.0,0,0,0. | 0.0000 | |
| 962 | 2013-10-31 | Thursday | 10211 | Taj Gibson | 10446.1... | Joakim No... | 0.8901.0... | 2,2,2,2,2... | 0.0,0,0,0. | 0.0000 | |
| 963 | 2013-11-21 | Thursday | 10211 | Taj Gibson | 10318.1... | Wesley Jo... | 0.8444.0... | 17,17,17... | 0.0,0,0,0. | 0.0000 | |
| 964 | 2013-12-05 | Thursday | 10211 | Taj Gibson | 10533.1... | Iman Shu... | 0.7222.0... | 30,33,30... | 0.0,0,0,0. | 0.0000 | |
| 965 | 2013-10-29 | Tuesday | 10211 | Taj Gibson | 10446.1... | Joakim No... | 0.8901.0... | 2,2,2,2,2... | 0.0,0,0,0. | 0.0000 | |
| 966 | 2014-03-13 | Thursday | 10211 | Taj Gibson | 10265.1... | J.J. Hickso... | 0.7222.0... | 56,58,48... | 1,0,1,1,0. | 0.0081 | |
| 967 | 2014-02-04 | Tuesday | 10211 | Taj Gibson | 10123.1... | Darren Col... | 0.7857.0... | 60,58,57... | 0.0,0,0,0. | 0.0000 | |
| 968 | 2013-12-02 | Monday | 10211 | Taj Gibson | 10533.1... | Iman Shu... | 0.7222.0... | 30,33,30... | 0.0,0,0,0. | 0.0000 | |
| 969 | 2013-12-05 | Thursday | 10595 | Beno Udrih | 10364.1... | Shaun Livi... | 0.8984.0... | 31,25,30... | 0.0,0,3,0. | 0.0246 | |
| 970 | 2014-01-05 | Sunday | 10595 | Beno Udrih | 10123.1... | Darren Col... | 0.8175.0... | 49,46,44... | 0.0,0,0,3. | 0.0274 | |
| 971 | 2013-11-10 | Sunday | 10595 | Beno Udrih | 10069.1... | Andrew B... | 0.9887.0... | 16,12,15... | 0.0,0,0,2. | 0.0000 | |
| 972 | 2014-01-03 | Friday | 10595 | Beno Udrih | 10123.1... | Darren Col... | 0.8175.0... | 49,46,44... | 0.0,0,0,3. | 0.0274 | |
| 973 | 2013-11-19 | Tuesday | 10595 | Beno Udrih | 10069.1... | Andrew B... | 0.9887.0... | 16,12,15... | 0.0,0,0,2. | 0.0000 | |
| 974 | 2013-12-08 | Sunday | 10595 | Beno Udrih | 10364.1... | Shaun Livi... | 0.8984.0... | 31,25,30... | 0.0,0,3,0. | 0.0246 | |
| 975 | 2014-03-15 | Saturday | 10595 | Beno Udrih | 10005.1... | Alexis Ajin... | 0.7222.0... | 49,64,70... | 0.0,0,1,2. | 0.0176 | |
| 976 | 2014-03-08 | Saturday | 10595 | Beno Udrih | 10005.1... | Alexis Ajin... | 0.7222.0... | 49,64,70... | 0.0,0,1,2. | 0.0176 | |
| 977 | 2014-01-02 | Thursday | 10595 | Beno Udrih | 10123.1... | Darren Col... | 0.8175.0... | 49,46,44... | 0.0,0,0,3. | 0.0274 | |
| 978 | 2014-04-13 | Sunday | 10595 | Beno Udrih | 10205.1... | Diante Gar... | 0.7222.0... | 71,54,79... | 0.1,0,1,2. | 0.0201 | |
| 979 | 2013-12-22 | Sunday | 10477 | Nikola Pek... | 10368.1... | Kevin Love... | 0.7577.0... | 30,22,32... | 0.0,0,0,6. | 0.0548 | |
| 980 | 2013-11-04 | Monday | 10477 | Nikola Pek... | 10280.1... | Dwight Ho... | 0.9010.0... | 18,16,10... | 0.0,2,0,0. | 0.0387 | |
| 981 | 2013-11-10 | Sunday | 10477 | Nikola Pek... | 10280.1... | Dwight Ho... | 0.9010.0... | 18,16,10... | 0.0,2,0,0. | 0.0387 | |
| 982 | 2013-11-19 | Tuesday | 10477 | Nikola Pek... | 10280.1... | Dwight Ho... | 0.9010.0... | 18,16,10... | 0.0,2,0,0. | 0.0387 | |
| 983 | 2014-01-21 | Tuesday | 10477 | Nikola Pek... | 10303.1... | Al Jefferso... | 0.7788.0... | 27,28,20... | 2,1,8,0,0. | 0.0563 | |
| 984 | 2014-01-27 | Monday | 10477 | Nikola Pek... | 10303.1... | Al Jefferso... | 0.7788.0... | 27,28,20... | 2,1,8,0,0. | 0.0563 | |
| 985 | 2013-12-15 | Sunday | 10477 | Nikola Pek... | 10368.1... | Kevin Love... | 0.7577.0... | 30,22,32 | 0.0,0,0,6. | 0.0548 | |
| 986 | 2013-11-03 | Sunday | 10477 | Nikola Pek... | 10280.1... | Dwight Ho... | 0.9010.0... | 18,16,10... | 0.0,2,0,0. | 0.0387 | |
| 987 | 2013-11-30 | Saturday | 10477 | Nikola Pek... | 10280.1... | Dwight Ho... | 0.9010.0... | 18,16,10... | 0.0,2,0,0. | 0.0387 | |
| 988 | 2014-03-11 | Tuesday | 10477 | Nikola Pek... | 10362.1... | Damian Lill... | 0.8260.0... | 75,75,45... | 0.0,1,0,0. | 0.0000 | |

INJURY PREDICTION REPORT
FIG. 2A

| FIG. 2A | FIG. 2B |
|---|---|

| Probability of Injury (Target Player) | # Games Played (Target Player) | # Injuries (Target Player) | Probability of Injury | Total Probability of Injury | Nearest Injury | # Days Free | Day of Nearest Injury | # Games Played | Target Injury | Target Injury | Pediction Accuracy |
|---|---|---|---|---|---|---|---|---|---|---|---|
| 0.0000 | 30 | 0 | 0.0000 | 0.0000 | 2014-11-01 | 317 | Saturday | 64 | 0 | 0 | 0 |
| 0.0000 | 2 | 0 | 0.0000 | 0.0000 | 2014-11-01 | 366 | Saturday | 82 | 0 | 0 | 0 |
| 0.0000 | 15 | 0 | 0.0000 | 0.0000 | 2014-11-01 | 345 | Saturday | 69 | 0 | 0 | 0 |
| 0.0000 | 30 | 0 | 0.0000 | 0.0000 | 2014-11-01 | 331 | Saturday | 54 | 0 | 0 | 0 |
| 0.0000 | 2 | 0 | 0.0000 | 0.0000 | 2014-11-01 | 368 | Saturday | 82 | 0 | 0 | 0 |
| 0.0081 | 74 | 0 | 0.0000 | 0.0040 | 2014-11-01 | 233 | Saturday | 10 | 0 | 0 | 0 |
| 0.0000 | 58 | 0 | 0.0000 | 0.0000 | 2014-11-01 | 270 | Saturday | 26 | 0 | 0 | 0 |
| 0.0000 | 30 | 0 | 0.0000 | 0.0000 | 2014-11-01 | 334 | Saturday | 54 | 0 | 0 | 0 |
| 0.0246 | 13 | 0 | 0.0000 | 0.0123 | 2014-01-11 | 37 | Saturday | 4 | 0 | 0 | 0 |
| 0.0274 | 17 | 2 | 0.0588 | 0.0431 | 2014-04-25 | 475 | Saturday | 53 | 0 | 0 | 0 |
| 0.0000 | 10 | 0 | 0.0000 | 0.0000 | 2014-01-11 | 62 | Saturday | 7 | 0 | 0 | 0 |
| 0.0274 | 17 | 2 | 0.0588 | 0.0431 | 2015-04-25 | 477 | Saturday | 53 | 0 | 0 | 0 |
| 0.0000 | 10 | 0 | 0.0000 | 0.0000 | 2014-01-11 | 53 | Saturday | 7 | 0 | 0 | 0 |
| 0.0246 | 13 | 0 | 0.0000 | 0.0123 | 2014-01-11 | 34 | Saturday | 4 | 0 | 0 | 0 |
| 0.0176 | 24 | 2 | 0.0417 | 0.0297 | 2015-04-25 | 406 | Saturday | 46 | 0 | 0 | 0 |
| 0.0176 | 24 | 2 | 0.0417 | 0.0297 | 2015-04-25 | 413 | Saturday | 46 | 0 | 0 | 0 |
| 0.0274 | 17 | 2 | 0.0588 | 0.0431 | 2015-04-25 | 478 | Saturday | 53 | 0 | 0 | 0 |
| 0.0201 | 27 | 2 | 0.0370 | 0.0286 | 2015-04-25 | 377 | Saturday | 43 | 0 | 0 | 0 |
| 0.0548 | 30 | 0 | 0.0000 | 0.0274 | 2014-01-28 | 37 | Tuesday | 4 | 0 | 0 | 0 |
| 0.0387 | 18 | 0 | 0.0000 | 0.0193 | 2014-01-28 | 85 | Tuesday | 16 | 0 | 0 | 0 |
| 0.0387 | 18 | 0 | 0.0000 | 0.0193 | 2014-01-28 | 79 | Tuesday | 16 | 0 | 0 | 0 |
| 0.0387 | 18 | 0 | 0.0000 | 0.0193 | 2014-01-28 | 70 | Tuesday | 16 | 0 | 0 | 0 |
| 0.0563 | 34 | 1 | 0.0294 | 0.0429 | 2014-03-16 | 54 | Sunday | 3 | 0 | 0 | 0 |
| 0.0563 | 34 | 1 | 0.0294 | 0.0429 | 2014-03-16 | 48 | Sunday | 3 | 0 | 0 | 0 |
| 0.0548 | 30 | 0 | 0.0000 | 0.0274 | 2014-01-28 | 44 | Tuesday | 4 | 0 | 0 | 0 |
| 0.0387 | 18 | 0 | 0.0000 | 0.0193 | 2014-01-28 | 86 | Tuesday | 16 | 0 | 0 | 0 |
| 0.0387 | 18 | 0 | 0.0000 | 0.0193 | 2014-01-28 | 59 | Tuesday | 16 | 0 | 0 | 0 |
| 0.0000 | 37 | 2 | 0.0541 | 0.0271 | 2014-11-19 | 253 | Wendesday | 2 | 0 | 0 | 0 |

INJURY PREDICTION REPORT

FIG. 2B

| SI NO. | OPTIMAL TH | PW | FPR | TPR | FNR | TNR | ACCURACY |
|---|---|---|---|---|---|---|---|
| 1 | 0.05 | 1 | 0.171 | 0.7 | 0.3 | 0.829 | 0.83 |
| 2 | | 2 | 0.171 | 0.58 | 0.42 | 0.829 | 0.83 |
| 3 | | 3 | 0.17 | 0.53 | 0.47 | 0.83 | 0.83 |
| 4 | | 4 | 0.17 | 0.46 | 0.54 | 0.83 | 0.83 |
| 5 | | 5 | 0.169 | 0.49 | 0.51 | 0.831 | 0.83 |
| 6 | | 6 | 0.168 | 0.49 | 0.51 | 0.832 | 0.83 |
| 7 | | 7 | 0.167 | 0.45 | 0.55 | 0.833 | 0.83 |
| 8 | | 8 | 0.167 | 0.45 | 0.55 | 0.833 | 0.83 |
| 9 | | 10 | 0.168 | 0.44 | 0.56 | 0.832 | 0.83 |
| 10 | | 12 | 0.168 | 0.42 | 0.58 | 0.832 | 0.83 |
| 11 | | 14 | 0.167 | 0.4 | 0.6 | 0.833 | 0.82 |

PREDICTION PERFORMANCE TABLE

FIG. 3

METHODS AND APPARATUS TO PREDICT SPORTS INJURIES

RELATED APPLICATIONS

This patent claims the benefit of U.S. Provisional Patent Application No. 62/409,707, filed on Oct. 18, 2016, and entitled, "Methods and Apparatus to Predict Sports Injuries," which is hereby incorporated herein by reference in its entirety.

FIELD OF THE DISCLOSURE

The present disclosure relates generally to machine-based data processing and, more particularly, to methods and apparatus to predict sports injuries.

BACKGROUND

Sports are played on many levels ranging from youth sports to national and international professional-level sports. In many levels of competition, player and team statistics are often collected to memorialize past player and team performances. Many fans use such statistics data to follow the progress of players and teams during a sports season. Such statistics can also be used by teams and/or the players to generate play/competition strategies, build teams, negotiate contracts, etc. In addition, such statistics can also be used by business organizations to make decisions on athlete sponsorships, team sponsorships, how to spend advertising dollars related to sporting events, etc.

BRIEF DESCRIPTION OF THE DRAWINGS

FIGS. 2A and 2B illustrate an example injury prediction report showing predictions of injuries for target participants.

FIG. 3 illustrates an example prediction performance table showing accuracies of injury predictions generated by the example apparatus of FIG. 1.

The figures are not to scale. Wherever possible, the same reference numbers will be used throughout the drawing(s) and accompanying written description to refer to the same or like parts.

DETAILED DESCRIPTION

Figure 1:
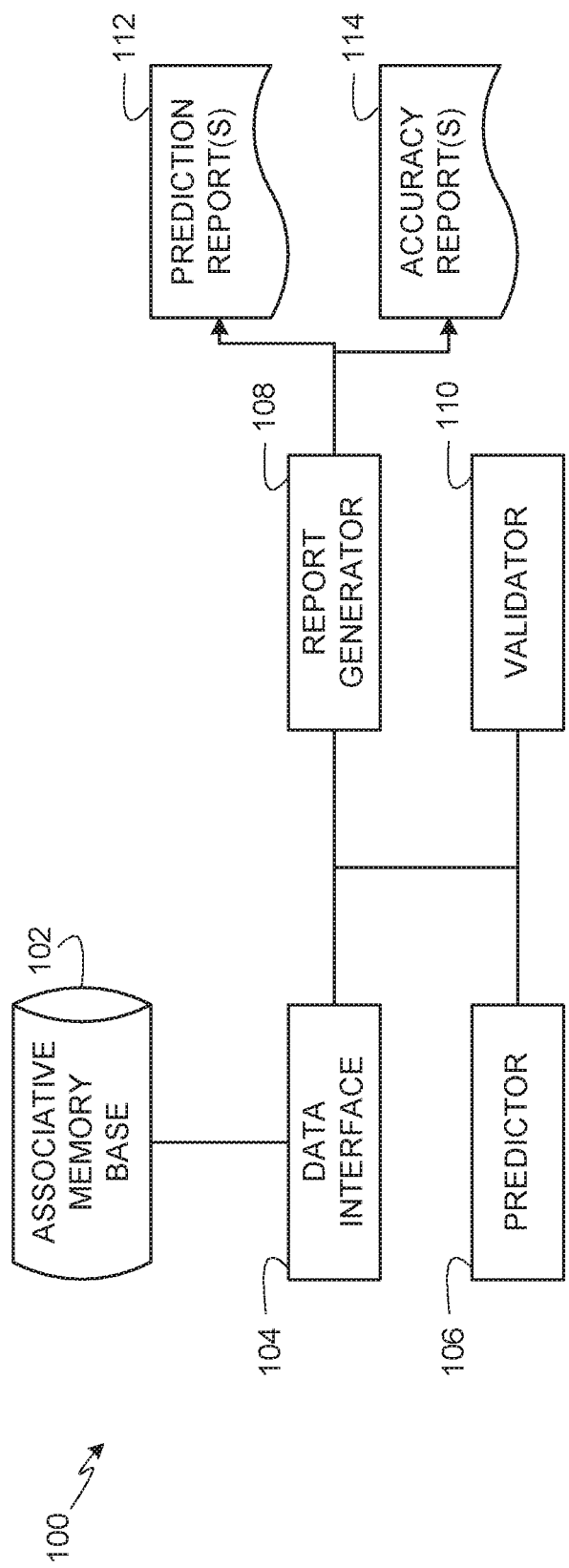
FIG. 1 depicts an example apparatus to predict sports injuries in accordance with the teachings of this disclosure.

Injuries of athletes (e.g., in-game/in-competition injuries) are quite common. Such injuries range from minor bruises to fatal injuries. Injuries affect the morale of the players and the team. Such injuries can also cause significant financial losses to the sports organizations by way of salary losses, medical expenses, losses due to reduced fan attendance, etc. Examples disclosed herein may be used to decrease the likelihood of injuries and/or the impact of such injuries on athletes, teams, and/or sports organizations by predicting probabilities of injuries of athletes based on analyses of athletic/sports records of other similar players identified by a cognitive framework.

Examples disclosed herein may be used to predict occurrences of sports injuries. Examples disclosed herein may be used for a number of different sports (e.g., basketball, baseball, American football, soccer/(international futbol), lacrosse, rugby, cricket, boxing, volleyball, swimming, tennis, track and field, etc. For example, techniques disclosed herein may be used to predict in-game injuries in a participant (e.g., an athlete, a player, a participant, etc.) before a particular game or competition. Disclosed examples include a predictive framework that uses cognitive technologies and methods to identify similar participants based on the similar participants' performance data such as competition achievements (e.g., number of points scored (goals, baskets, field goals, touchdowns, home runs, etc.), number of games played, etc.), fitness level (e.g., mechanical and physiological loads measured using accelerometers during a game/competition, an average run time, etc.), and/or injury records (e.g., number of past injuries).

Examples disclosed herein include a cognitive framework that uses an associative memory base (AMB) (e.g., an associative database that may be based on Saffron's associative memory base technology developed and provided by Saffron Technology of Los Altos, Calif., an Intel Company), which identifies similar participants based on associations of different attributes, measured using a Kolmogorov Complexity distance measure.

Disclosed examples predict the probability of injury of a target participant, based on the injury data distribution of a top number of N (e.g., five, or any other number) most similar athletes and similarity factors of those similar participants. The similarity factors of the similar athletes represent degrees of similarity between the similar athletes and the target participant. Example trials of the disclosed cognitive framework have been successfully conducted to predict injuries for National Basketball Association (NBA) players based on data from the 2013, 2014, and 2015 basketball seasons. However, examples disclosed herein may additionally or alternatively be used in connection with other sports.

Disclosed examples may be used to prevent player injuries, thus, enabling better team health and game schedule management. Disclosed examples may also be used to improve revenue generated by advertising, fan attendance and merchandising.

Disclosed examples leverage empirical evidence that in-game injuries in athletes are a byproduct of the athletes' physiological load and mechanical load. In examples disclosed herein, physiological load is an accumulative value representing physiological load on an athlete, involving distance traveled, average speed and the athlete's weight. In examples disclosed herein, mechanical load is an accumulative value representing mechanical load on an athlete's body and accelerations and decelerations. These factors are in-turn dependent upon a player's fitness level, which has a significant impact on the chances of the athlete sustaining an injury. Examples disclosed herein use athletes' histories of previous injuries as a predictor of future injuries.

Examples disclosed herein identify similar athletes to a target participant (e.g., a participant for whom an injury is being predicted), based upon a number of different performance data (e.g., competition achievements and/or fitness characteristics) over a prediction window (e.g., a previous number of day-range intervals such as the last 7, 14 and 30 days) leading up to a target game/competition date (e.g., target date of a game/competition for which an injury of the target participant is being predicted). Example performance data can include the cumulative physiological and mechanical loads, number of games played, points scored (e.g., goals, baskets, field goals, touchdowns, home runs, etc.), average run time in seconds, and/or any other performance data that can be collected/tracked for different players.

In examples disclosed herein, injury histories of the similar athletes, their similarity factors as measured using data in an associative memory base (AMB) platform, and the injury history of the target participant are used to predict the probability of injury of the target participant in a next prediction window (e.g., 7 days, 14 days, 21 days, etc.) leading up to a target game/competition date (e.g., a target date). In examples disclosed herein, a similarity factor is a percentage (e.g., a percent value) representative of how similar performance data parameters of a similar player are to corresponding performance data of a target player based on a Kolmogorov Complexity analysis (e.g., distances between player attributes). For example, the Kolmogorov Complexity analysis determines distances or differences between first player performance data parameters of the similar players and second player performance data parameters of the target players. In some examples, a similarity factor may additionally or alternatively represent a degree of similarity between performance data parameters of a similar player and corresponding performance data of a target player based on cosine similarity between attribute vectors (e.g., performance data) and/or based on frequencies or counts of co-occurrences of different attributes (e.g., the frequency or count of performance data being the same between the two players).

Examples disclosed herein are useful over prior solutions in a number of ways. For example, disclosed examples employ predictive analytics that are based on performance and fitness records of similar athletes relative to the target participant. As such, the predictive analytics are adaptive and useful for real-time analysis while new performance data is being annotated, updated, and/or added because there is no requirement for offline, or prior, training on annotated data, updated data, and/or new data. Examples disclosed herein offer improvements in accuracy and computation efficiency over prior methods based on traditional machine learning techniques that do require such offline, or prior, training on annotated data, updated data, and/or new data.

In addition, since the disclosed examples do not rely on a pre-learned model, the disclosed examples are highly flexible with respect to, among other aspects, adding or removing attributes or changing similarity measuring parameters. Also, since examples disclosed herein are not based on traditional classification methods, the disclosed examples provide comparatively much better performance under unbalanced or sparse data. For example, results generated by examples disclosed herein provide a 70% true-positive rate with just 1.6% positive samples in data.

Unlike prior model-based methods, examples disclosed herein are not only based on injury data distribution of similar athletes, but also take into consideration injury history of target participants. As such, accuracies of injury predictions are increased using examples disclosed herein. In test cases using examples disclosed herein, 80% prediction accuracy was achieved in predicting injuries for NBA players based on sports data provided by Kinduct Technologies of Halifax, Nova Scotia, Canada.

In addition, examples disclosed herein employ a rich sports database and provide improved injury predictions over time as more records of athletes' data are added. Such improvements in injury prediction accuracy based on added data records are achieved without any additional effort or human intervention, as the cognitive framework of the disclosed examples need not be re-trained or updated.

FIG. 1 depicts an example apparatus 100 to predict sports injuries in accordance with the teachings of this disclosure. The example apparatus 100 includes an example data interface 104, an example predictor 106, an example report generator 108, and an example validator 110. In the illustrated example, the data interface 104 is in communication with an associative memory base (AMB) 102 and may query the AMB 102 using, for example, JavaScript, python, etc. The example AMB 102 is an associative database or data structure that stores player performance data parameters in an associative manner on a large number of players that participate in a sports league. Example player performance data parameters include physiological load (physio_load), mechanical load (mechanical_load), mechanical intensity (mechanical_intensity), physical intensity (physical_intensity), number of games played (games_played), average running seconds (avg_seconds), average field goals (avg_field_goals), previous injuries (prev_injuries), position played, seconds played, average/moving average of seconds played, seconds played from a previous season, venue played, venue floor type, specific competitive division, venue temperature, player temperature, perspiration amount, type of shoes worn, types of protective gear worn, injuries incurred against particular opponents, opponent's playing style (e.g., offensive alignment, defensive alignment), player age, player's physical attributes (e.g., height, weight, arm reach, finger length, body mass index (BMI), electrocardiogram (ECG) measures, diastolic blood pressure, systolic blood pressure, etc.), all-star status, most valuable player (MVP) status, playing style (e.g., offensive, defensive, aggressive, high-contact play, low-contact play, shot blocking, etc.). In other examples, fewer, more, and/or different performance data parameters may be stored by the AMB 102 for use in accordance with the teachings of this disclosure. In some examples, performance data parameters can be selected for use with techniques disclosed herein based on empirical analysis of what types of performance data produce high prediction accuracies for sports injuries. In some examples, some performance data parameters may be selected based on whether they contribute to a player's level of muscle fatigue. In some examples, performance data parameters may be selected based on secondary effects that may create higher probabilities of injury. For example, venue temperature, player temperature, and/or perspiration amount may be indicative of excessive player perspiration that creates slippery floors, which could lead to higher probabilities of slip and fall injuries. In some examples, performance data parameters may include the ability of venue staff to address venue conditions (e.g., slippery floors, humidity, temperature, etc.) in an effective manner to lessen the likelihood of sports injuries arising from such venue conditions. Examples disclosed herein use relationship strengths (e.g., similarities) between the player performance data parameters of different players represented in the AMB 102 to predict probabilities of sports injuries of target players. The AMB 102 may be implemented using Saffron's associative memory base technology developed and provided by Saffron Technology. In some examples, the AMB 102 is part of the apparatus 100, while in other examples the AMB 102 is implemented separate from the apparatus 100.

The data interface 104 of the illustrated example obtains a number of player performance data parameter values for target participants and similar athletes from the AMB 102. In the illustrated example, the data interface 104 obtains data from the AMB 102 for a specified number (e.g., five) of most similar athletes (e.g., athletes most similar in performance data to the target participant). The AMB 102 of the illustrated example measures similarities between the target participant's records and records of other players represented in the database based on associations measured using Kolmogorov Complexity and returns identifiers (IDs) of the specified number of most similar athletes along with their similarity factors.

The example predictor 106 performs predictive analytics, which computes the probability of in-game injury of the target participant based on the performance data parameters of the target participant and similar athletes (e.g., past injuries, game records, etc. of the target participant and the similar athletes) obtained by the data interface 104 from the AMB 102, and based on the similarity factors between the target participant and the similar athletes.

The example report generator 108 generates example injury prediction reports 112 providing probabilities of injuries of target participants predicted by the predictor 106 for target game/competition dates. An example injury prediction report 112 is shown in FIGS. 2A and 2B. Turning briefly to FIGS. 2A and 2B, fields in the example injury prediction report 112 include target date 202, weekday of target date 204, target player ID 206, target player name 208, similar players ID 210, similar players names 212, similarity matrix 214, # of games played by similar players 216, # of injuries of similar players 218, probability of injury based on similar players 220, # games played by target player until target date 222, # of injuries of target player until target date 224, probability of injury based on target player's history 226, total probability of injury based on similar and target player 228, date of first injury 230, # of days from target date to first injury date 232, week day first injury reported 234, # of games played by target player before first injury and after target date 236, target injury prediction 238, target injury status with 7-day prediction window 240, and prediction accuracy 242. In other examples, the injury prediction report 112 may have fewer, more, and/or different data fields.

Returning to FIG. 1, the example report generator 108 also generates example accuracy reports 114 on the accuracies of past predictions. For example, after a target game/competition date, the validator 110 assesses the accuracies of injury predictions determined by the predictor 106 for target participants on the target game/competition date. After determining accuracies, the report generator 108 can generate the accuracy reports 114 showing percentages or degrees of accuracy between the injury predictions and actual injuries of target participants. Example data that may be generated by the validator 110 for such accuracy reports 114 is shown in the example prediction performance table 300 of FIG. 3.

While an example manner of implementing the apparatus 100 is illustrated in FIG. 1, one or more of the elements, processes and/or devices illustrated in FIG. 1 may be combined, divided, re-arranged, omitted, eliminated and/or implemented in any other way. Further, the example AMB 102, the example data interface 104, the example predictor 106, the example report generator 108, the example validator 110 and/or, more generally, the example apparatus 100 of FIG. 1 may be implemented by hardware, software, firmware and/or any combination of hardware, software and/or firmware. Thus, for example, any of the example AMB 102, the example data interface 104, the example predictor 106, the example report generator 108, the example validator 110 and/or, more generally, the example apparatus 100 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example AMB 102, the example data interface 104, the example predictor 106, the example report generator 108, and/or the example validator 110 is/are hereby expressly defined to include a tangible computer readable storage device or storage disk such as a memory, a digital versatile disk (DVD), a compact disk (CD), a Blu-ray disk, etc. storing the software and/or firmware. Further still, the example apparatus 100 may include one or more elements, processes and/or devices in addition to, or instead of, those illustrated in FIG. 1, and/or may include more than one of any or all the illustrated elements, processes and devices.

FIGS. 3-6 show results of predictive analytics performed by the example apparatus 100 of FIG. 1 for different prediction windows. In the illustrated examples, a true-positive rate (TPR) of 70% was achieved using highly unbalanced data (e.g., 1.6% positive cases). FIG. 3 illustrates an example prediction performance table 300 showing accuracies of injury predictions generated by the example apparatus 100. In table 300, different sports injury prediction accuracies are shown in a number of rows for different prediction IDs (e.g., prediction IDs labeled as SI No. in FIG. 3). The example table 300 includes an example optimal threshold (TH) column 302, an example prediction window (PW) column 304, an example false-positive rate (FPR) column 306, an example true-positive rate (TPR) column 308, an example false-negative rate (FNR) column 310, an example true-negative rate (TNR) column 312, and an example accuracy column 314. The example optimal threshold column 302 includes thresholds that are used to designate the absence or presence of the future injury. For example, an optimal threshold of 0.05 indicates that a probability of injury less than 0.05 is indicative of no future injury, whereas a probability of injury equal to or greater than 0.05 is indicative of the occurrence of a future injury. The example PW column 304 includes prediction windows, which are day-range windows extending between the date a prediction is made and a target date of a game/competition. Different prediction windows may be based on the number of days (e.g., a days-range) before a target game/competition date that results in the most accurate predictions.

The example FPR column 306 includes numbers that represent false indicators of positive rates for propensities of injury. The example TPR column 308 includes numbers that represent true indicators of positive rates for propensities of injury. The example FNR column 310 includes numbers that represent false indicators of negative rates for propensities of injury. The example TNR column 312 includes numbers that represent true indicators of negative rates for propensities of injury. The example accuracy column 314 includes percentages of accuracies between predicted injuries and confirmed occurrences of injuries.

The example rates (FPR, TPR, FNR, TNR) shown in the table 300 of FIG. 3 are representative of ratios of cases when injuries were or were not predicted divided by cases when such predicted injuries did or did not occur. For example, an FPR is representative of a ratio of injuries that were predicted relative to actual non-occurrences of one or more of those injuries in a game/competition. A TPR is representative of a ratio of injuries that were predicted relative to actual occurrences of one or more of those injuries. An FNR is representative of a ratio of injuries not predicted relative to actual occurrences of one or more of those injuries. A TNR is representative of a ratio of injuries not predicted relative to actual non-occurrences of one or more of those injuries.

In the illustrated example of FIG. 3, TPR is very high (70%) with one day as a prediction window. In the example associative memory base 102 of FIG. 1, player injuries are not linked to corresponding games. As such, injuries reported within one day after a game date are considered to have occurred on that game date. In addition, validations of injury predictions show that injury predictions generated using a one day prediction window have a high level of accuracy. Also, FNR is lowest when the prediction window is between 1-3 days (30%-47%) before a target game/competition date. In addition, FPR is very good for all prediction windows (~17%). The difference is not significant (e.g., the variation in FPR among different prediction windows shows a decrease from ~19% (with all injuries) to ~17%). In the illustrated example, the removal of contact injuries removed noise from data by increasing credibility of injury cases, hence increasing TPR and reducing FPR.

Figure 4:
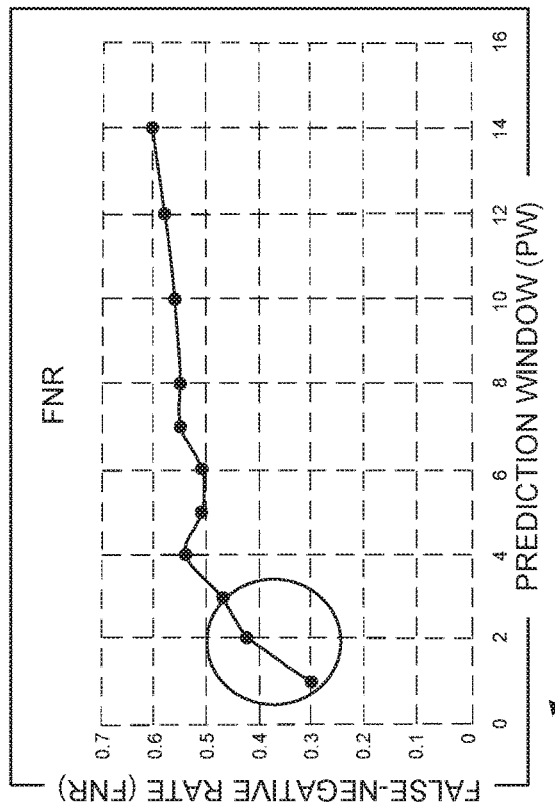
FIG. 4 illustrates an example graph showing true-positive rates (TPRs) relative to corresponding injury predictions determined by the example apparatus of FIG. 1.
Figure 5:
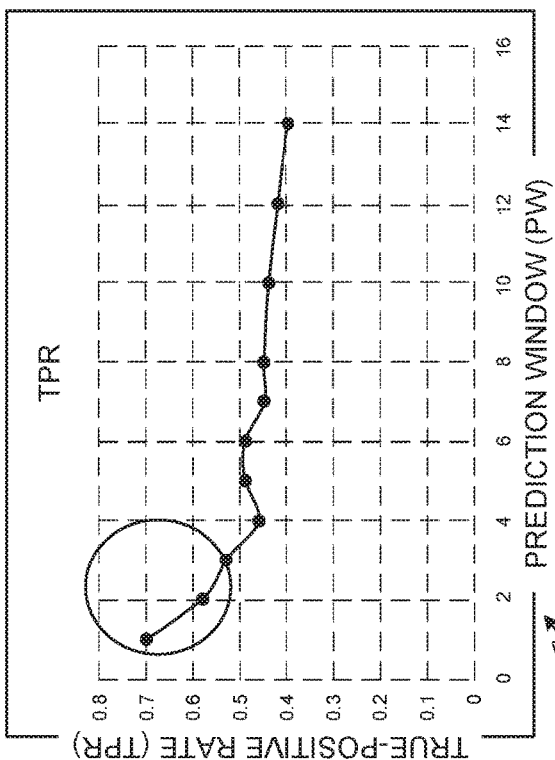
FIG. 5 illustrates an example graph showing false-negative rates (FNRs) relative to corresponding injury predictions determined by the example apparatus of FIG. 1.
Figure 6:
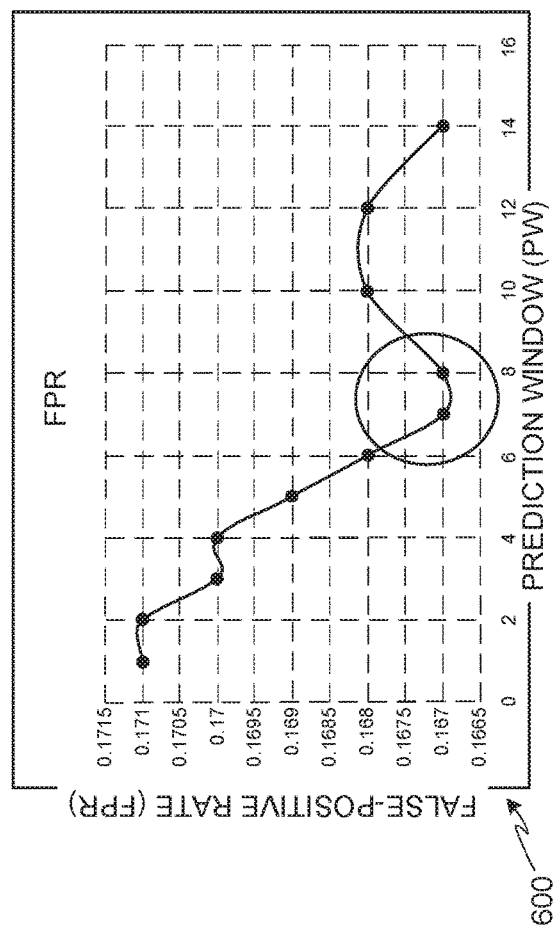
FIG. 6 illustrates an example graph showing false-positive rates (FPRs) relative to corresponding injury predictions determined by the example apparatus of FIG. 1.

FIG. 4 illustrates an example TPR graph 400 showing TPRs relative to corresponding injury predictions determined by the example apparatus 100 of FIG. 1. In the example TPR graph 400, higher TPRs (circled) show better predictions. In the illustrated example of FIG. 4, the TPR was the highest with one day as a prediction window spanning the date on which the prediction was determined and the target game/competition date for which the in-game injury was predicted. FIG. 5 illustrates an example FNR graph 500 showing FNRs relative to corresponding injury predictions determined by the example apparatus 100 of FIG. 1. In the example FNR graph 500, lower TPRs (circled) show better predictions. FIG. 6 illustrates an example FPR graph 600 showing FPRs relative to corresponding injury predictions determined by the example apparatus 100 of FIG. 1. In the example FPR graph 600, lower FPRs (circled) show better predictions.

Examples disclosed herein were tested and proven on around 8000 game date and player combinations from an NBA sports database (e.g., the AMB 102 of FIG. 1). The disclosed example predictive framework predicted injuries in players based on top most similar players obtained following an all-but-one selection methodology. The disclosed examples predicted injuries of players with 83% accuracy in a wide range of prediction windows spanning 1-14 days.

Examples disclosed herein can be extended to include any number of similar athletes and different parameters from the AMB 102 for identifying similar athletes such as from opponent teams, etc. In addition, probability of injury calculations can be modulated to account for different time periods in a sport season. For example, injuries can be more likely during the latter part of a season.

Figure 7:
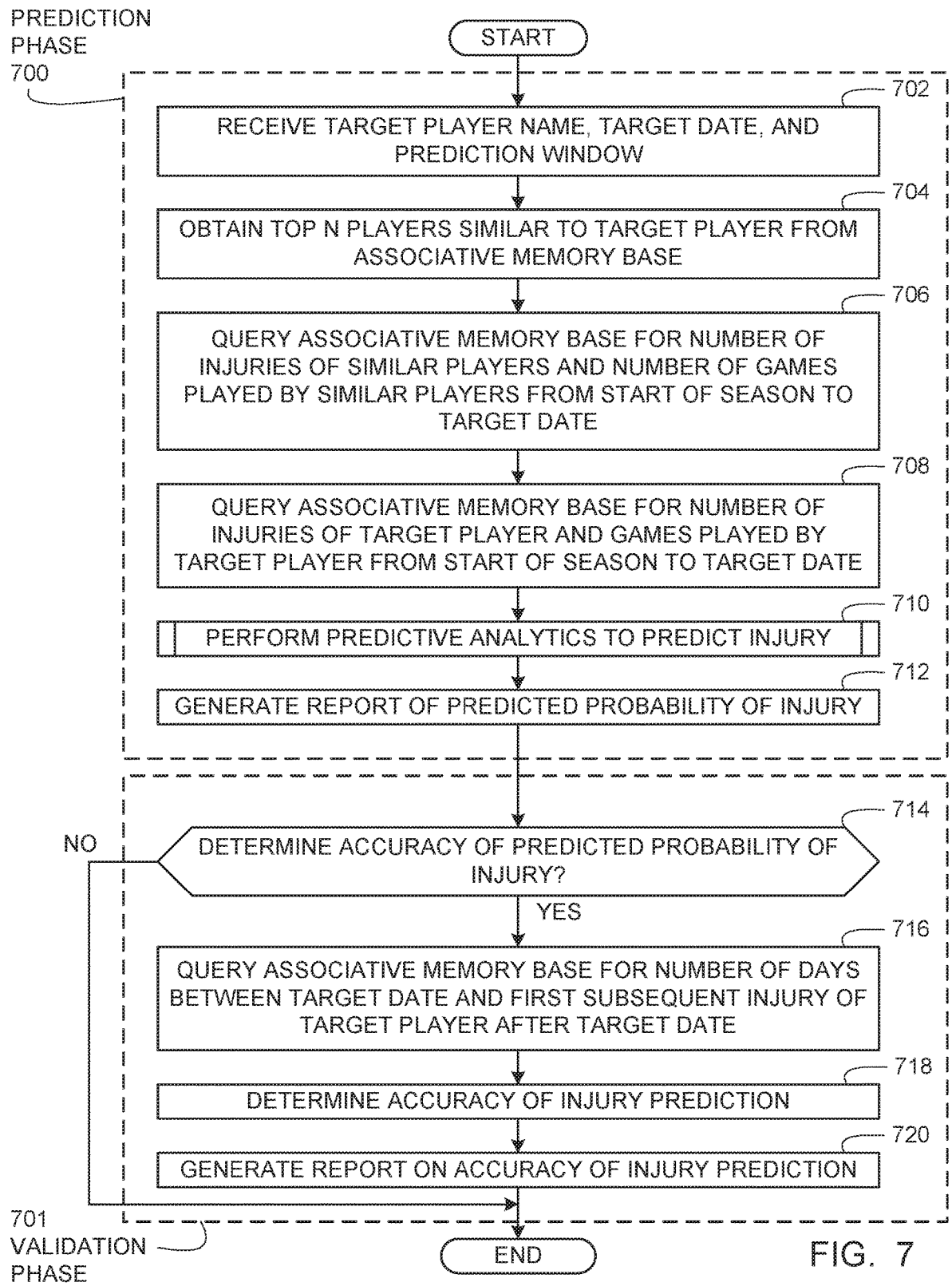
FIG. 7 is a flow diagram representative of example machine readable instructions that may be executed by a processor to predict and/or validate probabilities of sports injuries in accordance with the teachings of this disclosure.

FIG. 7 is a flow diagram representative of example machine readable instructions that may be executed by a processor (e.g., the example processor 912 of FIG. 9) to predict and/or validate probabilities of sports injuries in accordance with the teachings of this disclosure. The example process of FIG. 7 is separated into two phases, namely a prediction phase 700 and a validation phase 701. In the prediction phase 700, the example predictor 106 of FIG. 1 predicts injuries of target participants for target dates (e.g., target game dates, target competition dates, etc.) based on predictive analytics of performance data collected for a current sport's season (e.g., from a start of the sport's season to a target date). In the validation phase 701, the validator 110 determines accuracies of the injury predictions after the target dates have passed.

Turning in detail to FIG. 7, initially, during the prediction phase 700, the example predictor 106 (FIG. 1) receives a target player name, a target date, and a prediction window (block 702). The example data interface 104 obtains the top N players similar to the target player from the AMB 102 (block 704). For example, the data interface 104 may query the AMB 102 (e.g., using JavaScript, python, etc.) to find the top N players that are most similar to the target player. In the illustrated example, the AMB 102 can use a priority ranking of the similar players using a Kolmogorov complexity metric based on similarities in cumulative values of performance data parameters over the last 7, 14, and 21 days within a sport's season before a target date. In this manner, at block 704, the data interface 104 can receive from the AMB 102 the player IDs of the selected top N players having more similarities with the target player based on the performance data parameters than other players in the AMB 102. The periodic intervals of 7, 14, and 21 days for which to access performance data are examples that may be selected to increase the accuracies of injury predictions for subsequent games. Any other suitable intervals may be used based on desired levels of accuracy and available data to suit the needs of particular implementations. In the illustrated example, the selecting of the top N similar players is based on a priority ranking of performance data parameters. An example two-level priority ranking of performance data parameters that may be employed for selecting the top N similar players at block 704 is provided as follows in association with performance data parameters (a)-(g), is: (a) physiological load (physio_load) (priority level 1), (b) mechanical load (mechanical_load) (priority level 1), (c) mechanical intensity (mechanical_intensity) (priority level 2), (d) physical intensity (physical_intensity) (priority level 1), (e) number of games played (games_played) (priority level 1), (f) average running seconds (avg_seconds) (priority level 1), and (g) average field goals (avg_field_goals) (priority level 1). In some examples, fewer, more, and/or other performance data parameters may be employed. In addition, any number of priority levels may be employed, and the priority order of the performance data parameters may be changed.

The example data interface 104 queries the AMB 102 for the number of injuries of the similar players and the number of games played by the similar players from the start of a season to the target date (block 706). The example data interface 104 queries the AMB 102 for the number of injuries of the target player and the number of games played by the target player from the start of the season to the target date (block 708). The example predictor 106 (FIG. 1) performs predictive analytics on the obtained data to predict an injury of the target player (block 710). An example process that may be used to implement the predictive analytics of block 710 is described below in connection with the flow diagram of FIG. 8. The example report generator 108 (FIG. 1) generates a report of the predicted probability of injury of the target player on the target date (block 712). For example, the report generator 108 can generate the injury prediction report 112 of FIGS. 1, 2A, and 2B.

During a validation phase 701 after the target date (e.g., the game/competition has been played), the example validator 110 (FIG. 1) determines whether to determine an accuracy of a predicted probability of injury (block 714). If the validator 110 determines that it should determine the accuracy of a predicted probability of injury (block 714), the example data interface 104 queries the AMB 102 for the number of days between the target date and a first subsequent injury of the target player after the target date (block 716). The validator 110 determines the accuracy of the injury prediction (block 716). For example, the validator 110 determines the accuracy of the injury prediction based on the number of days before the most recent injury of the target player after the target date accessed at block 716. The example report generator 108 generates an accuracy report 114 (FIG. 1) on the accuracy of the injury prediction (block 720). For example, the accuracy report 114 can include data shown in the prediction performance table 300 FIG. 3. After generating the accuracy report 114 or if the validator 110 determines a block 714 to not determine the accuracy of a predicted probability of injury, the example process of FIG. 7 ends.

Figure 8:
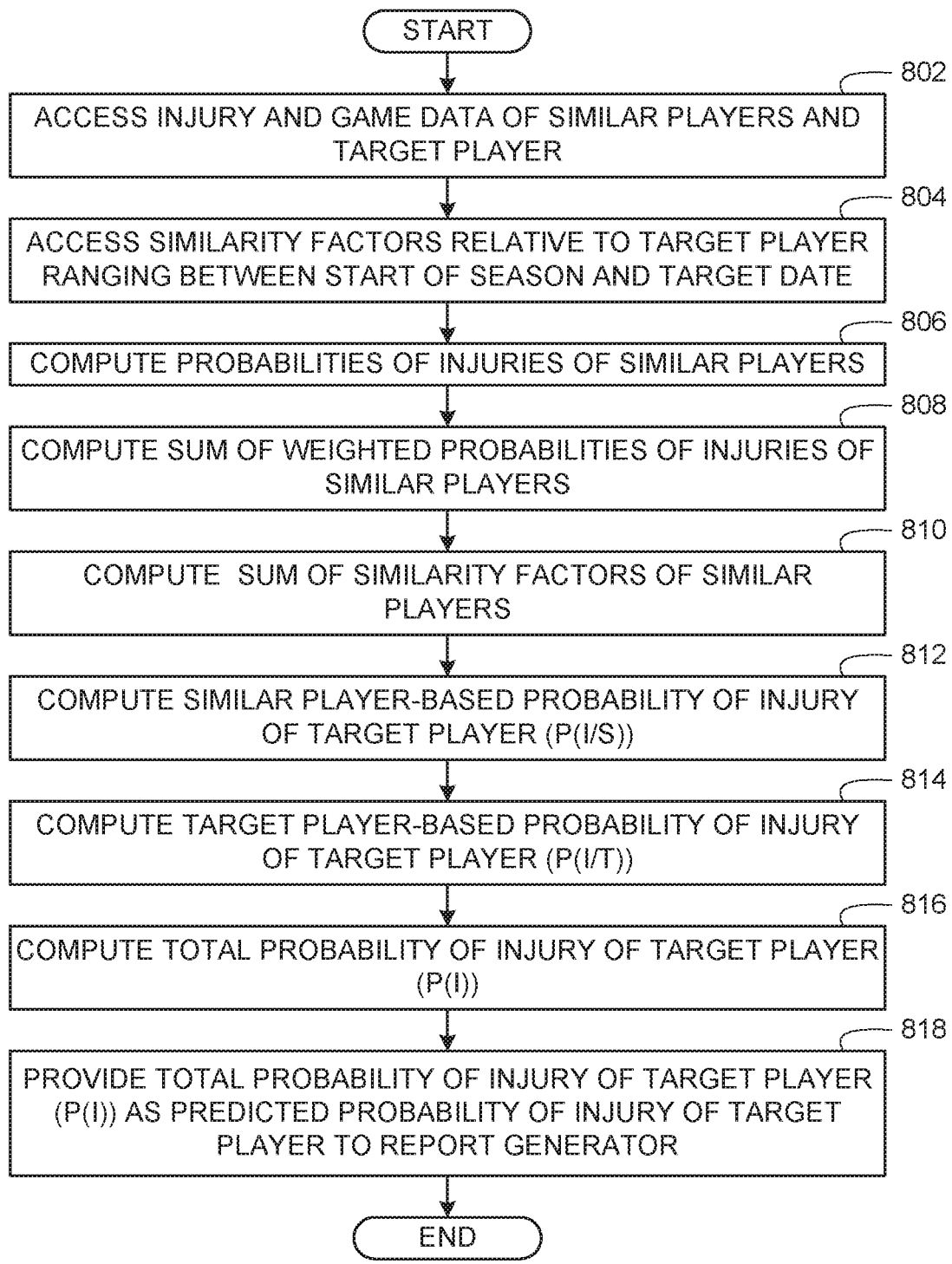
FIG. 8 is a flow diagram representative of example machine readable instructions that may be executed by a processor to perform a predictive analytics process to predict probabilities of sports injuries in accordance with the teachings of this disclosure.

FIG. 8 is a flow diagram representative of example machine readable instructions that may be executed by a processor (e.g., the example processor 912 of FIG. 9) to perform a predictive analytics process to predict probabilities of sports injuries in accordance with the teachings of this disclosure. The example process of FIG. 8 may be used to perform the predictive analytics of block 710 of FIG. 7. The predictive analysis of FIG. 8 computes the probability of injury of similar players (P(S)) weighted with similarity factors (M) with respect to the target player. The sum of these weighted probabilities normalized with the sum of the similarity factors (M) provides a similar player-based probability of injury of the target player (e.g., a probability of injury for the target player based on performance data of the similar players which represented by the notation P(I/S)). For example, if the probability of injury of all similar players is one, then the similar player-based probability of injury of the target player (P(I/S)) would be one, and if the probability of injury of all similar players is zero, the similar player-based probability of injury of the target player (P(I/S)) would also be zero. For all other values, the similar player-based probability of injury of the target player (P(I/S)) would be between 0 and 1.

Research conducted in the development of techniques disclosed herein shows that a previous injury is a good predictor of injury. Hence, the predictive analysis disclosed herein also computes the injury trend of the target player and computes the total probability of injury of the target player (P(I)) (i.e., the predicted probability of injury of the target player) based on a combination of the similar player-based probability of injury of the target player (P(I/S)) (e.g., a probability of injury of the target player based on performance data of the similar players) and a target player-based probability of injury of the target player (P(I/T)) (e.g., a probability of injury of the target player based on performance data of the target player).

Initially in FIG. 8, the example predictor 106 accesses injury and game data of similar players and the target player (block 802). For example, the predictor 106 accesses injury and game data of similar players and the target player from a start of a current season to a target date. The example predictor 106 also accesses similarity factors (M) relative to the target player ranging between the start of the season and the target date (block 804). The example predictor 106 computes the probabilities of injuries of the similar players (block 806). In the illustrated example, the predictor 106 determines a probability of injury for each similar player (P(S)) based on the number of games played and the number of injuries of that corresponding similar player between the start of the sport's season and the target date. For example, the predictor 106 determines the probability of injury of a similar player (P(S)) by dividing a number of injuries of the similar player by the number of games played by the similar player (e.g., P(S)=number of injuries of similar player/number of games played by the similar player). In this manner, for each similar player, the example predictor 106 determines an average number of injuries per game that can be used as the probability of that similar player getting injured (P(S)) in a next game.

The example predictor 106 computes the sum of weighted probabilities of injuries of the similar players (P(S)M) (block 808). For example, the predictor 106 computes the sum of weighted probabilities of injuries of the similar players (P(S)M) by multiplying each probability of injury of each similar player (P(S)) determined at block 806 by a corresponding similarity factor (M) of that similar player, and summing the weighted probabilities of injuries of the similar players (P(S)M). In the illustrated example, the predictor 106 uses Equation 1 below to compute the sum of weighted probabilities of injuries of the similar players (P(S)M) of block 808.

$$P(S)M = \Sigma_{(i=1:N)}(P(S(i))*M(i)) \quad \text{Equation 1}$$

In example Equation 1 above, the sum of weighted probabilities of injuries of the similar players (P(S)M) is determined based on the probability of injury of each similar player (P(S(i))) and the similarity factor (M(i)) for that similar player for a number of i=N similar players. That is, the sum of weighted probabilities of injuries of the similar players (P(S)M) is determined as a sum of the products of: (1) the probability of injury of each similar player (P(S)) and (2) the similarity factor (M) of that similar player. The probability of injury of each similar player (P(S(i))) used in example Equation 1 above is determined at block 806 for the current sport's season. By using example Equation 1, the probability of injury of each similar player (P(S)) is weighted by the corresponding similarity factor (M) for that similar player so that each probability of injury of a similar player (P(S)) can be used as a component in determining the probability of injury of a target player based on the similarity (e.g., the weighting by the similarity factor (M)) between that similar player and the target player.

The example predictor 106 computes the sum of the similarity factors of the similar players (block 810). In the illustrated example, the predictor 106 determines the sum of the similarity factors (M) of the similar players using Equation 2 below.

$$\text{Sum of the similarity factors}(M) = \Sigma_{(i=1:N)}M(i) \quad \text{Equation 2}$$

In Equation 2 above, the sum of the similarity factors (M) of the similar players is a summation of the similarity factors (M(i)) for a number of i=N similar players. For example, the sum of the similarity factors (M) of the similar players is a sum of percentages representative of amounts of similarity between performance data parameters of a similar player for a current sport's season and performance data parameters of a target player. The percentages can be based on a Kolmogorov Complexity analysis of (e.g., distances between player attributes).

The example predictor 106 computes a similar player-based probability of injury of the target player (P(I/S)) (block 812). In the illustrated example, the predictor 106 computes a similar player-based probability of injury of the target player (P(I/S)) using Equation 3 below.

$$P(I/S) = \frac{\sum_{(i=1:N)} (P(S(i))) * M(i)}{\sum_{(i=1:N)} M(i)} \qquad \text{Equation 3}$$

In example Equation 3 above, the similar player-based probability of injury of the target player (P(I/S)) is determined by dividing the sum of weighted probabilities of injuries of the similar players (e.g., $\Sigma_{(i=1:N)}(P(S(i))*M(i))$ determined at block 808 above by the sum of the similarity factors of the similar players $\Sigma_{(i=1:N)}(P(S(i))*M(i))$ determined at block 810 above (e.g., P(I/S)=(sum of the weighted probabilities of injuries of the similar players from start of season to target date)/(sum of the similarity factors of the similar players)). In some examples, the example predictor 106 predicts the similar player-based probability of injury of the target player at block 812 by treating the target player like a representative similar player based on the collective similar players (e.g., a virtual player that is similar to or representative of the collective similar players) as a result of the operation of block 812 being based on characteristics of the similar players (e.g., the injury and game data of each similar player accessed at block 802, and the similarity factors of the similar players accessed at block 804). In such examples, the similar player-based probability of injury for a representative similar player is used as the similar player-based probability of injury for the target player.

The example predictor 106 computes a target player-based probability of injury of the target player (P(I/T)) (block 814). For example, the predictor 106 determines the target player-based probability of injury of the target player (P(I/T)) by dividing the number of injuries of the target player by the number of games played by the target player from the start of the season to the target date (e.g., (P(I/T))=(number of injuries of the target player from the start of the season to the target date)/(number of games played by the target player from the start of the season to the target date)). The example predictor 106 computes the total probability of injury of the target player (P(I)) (block 816). In the illustrated example, the predictor 106 determines the total probability of injury of the target player (P(I)) based on a combination of the similar player-based probability of injury for the target player (P(I/S)) and the target player-based probability of injury of the target player (P(I/T)). For example, a linear combination of the similar player-based probability of injury for the target player (P(I/S)) and the target player-based probability of injury of the target player (P(I/T)) may be determined by determining the sum of P(I/S) and P(I/T), and dividing the sum by two (i.e., Linear Combination=(P(I/S)+P(I/T))/2). In other examples, nonlinear combinations of the similar player-based probability of injury for the target player (P(I/S)) and the target player-based probability of injury of the target player (P(I/T)) may additionally or alternatively be employed to determine the total probability of injury of the target player (P(I)) at block 816. For example, a nonlinear combination may be used by determining a square root (or any root) of the similar player-based probability of injury for the target player (P(I/S)) and adding the result to the target player-based probability of injury of the target player (P(I/T)). In yet other examples, other techniques for determining a combination of the probability of injury for the target player based on the similar players (P(I/S)) and the probability of injury of the target player (P(I/T)) may be employed at block 816. In the illustrated example, the predictor 106 provides the total probability of injury of the target player (P(I)) as the predicted probability of injury of the target player to the report generator 108 (block 818). In this manner, the example report generator 108 can generate the prediction report 112 (FIG. 1) at block 712 of FIG. 7 to include the total probability of injury of the target player determined at block 816 as the predicted probability of injury of the target player for the target date. The example process of FIG. 8 then ends, and control is passed back to a calling function or process such as the example process of FIG. 7.

In the above examples of FIGS. 7 and 8, the machine readable instructions comprise one or more programs for execution by a processor such as the processor 912 shown in the example processor platform 900 discussed below in connection with FIG. 9. The program(s) may be embodied in software stored on a tangible computer readable storage medium such as a CD-ROM, a floppy disk, a hard drive, a digital versatile disk (DVD), a Blu-ray disk, or a memory associated with the processor 912, but the entire program and/or parts thereof could alternatively be executed by a device other than the processor 912 and/or embodied in firmware or dedicated hardware. Further, although the example programs are described with reference to the flowcharts illustrated in FIGS. 7 and 8, many other methods of implementing the example apparatus 100 of FIG. 1 may alternatively be used. For example, the order of execution of the blocks may be changed, and/or some of the blocks described may be changed, eliminated, or combined.

As mentioned above, the example processes of FIGS. 7 and 8 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIGS. 7 and 8 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

Figure 9:
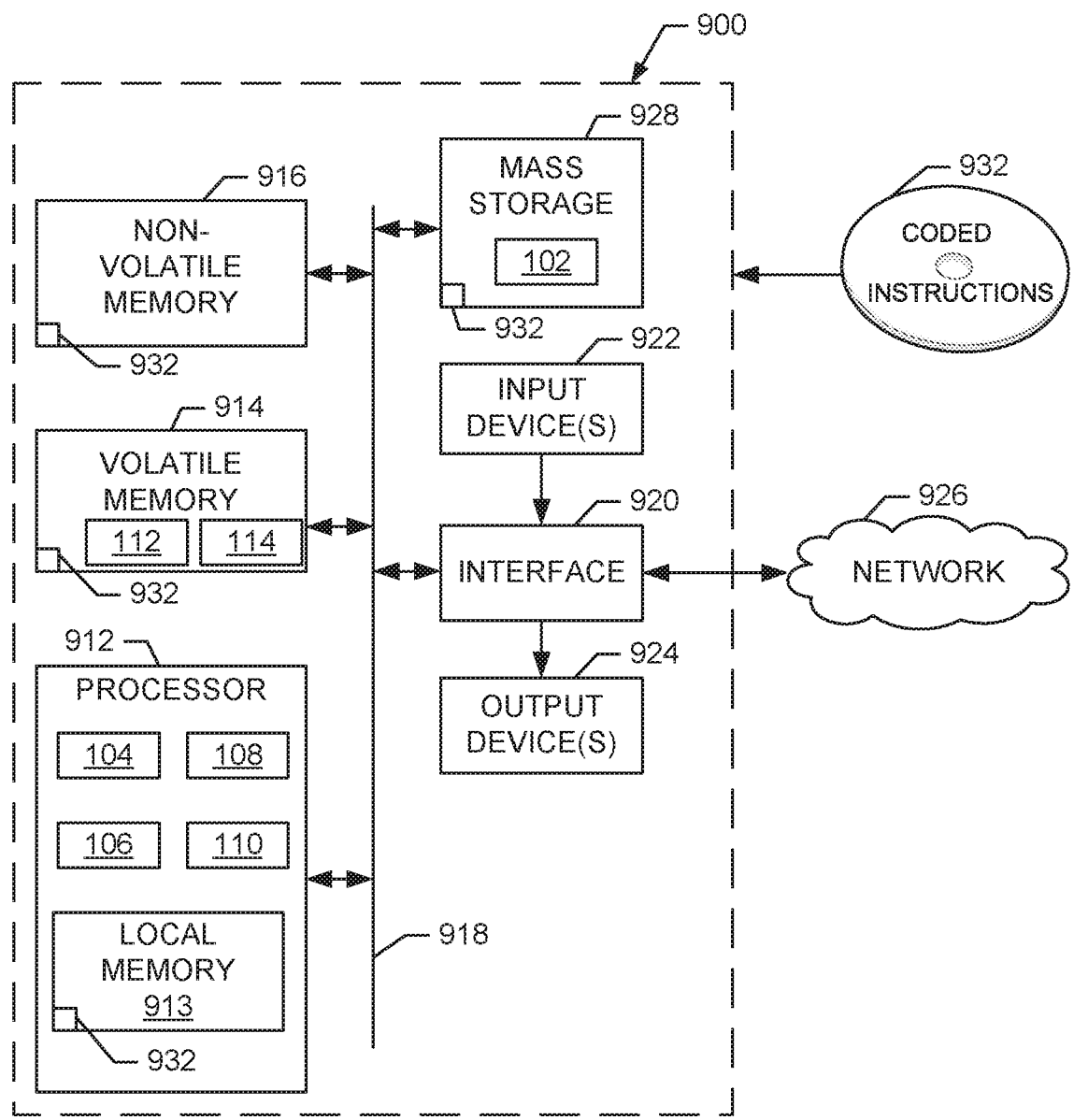
FIG. 9 is an example processor platform capable of executing the example computer readable instructions represented by FIGS. 7 and 8 to implement the example apparatus of FIG. 1 in accordance with teachings of this disclosure to predict and/or validate probabilities of sports injuries.

FIG. 9 is a block diagram of an example processor platform 900 capable of executing the instructions of FIGS. 7 and 8 to implement the example apparatus 100 of FIG. 1. The processor platform 900 can be, for example, a server, a personal computer, a mobile device (e.g., a cell phone, a smart phone, a tablet such as an iPad™), a personal digital assistant (PDA), an Internet appliance, a DVD player, a CD player, a digital video recorder, a Blu-ray player, a gaming console, a personal video recorder, a set top box, or any other type of computing device.

The processor platform 900 of the illustrated example includes a processor 912. The processor 912 of the illustrated example is hardware. For example, the processor 912 can be implemented by one or more integrated circuits, logic circuits, microprocessors or controllers from any desired family or manufacturer. In the illustrated example, the processor 912 implements the example data interface 104, the example predictor 106, the example report generator 108, and the example validator 110 of FIG. 1.

The processor 912 of the illustrated example includes a local memory 913 (e.g., a cache). The processor 912 of the illustrated example is in communication with a main memory including a volatile memory 914 and a non-volatile memory 916 via a bus 918. The volatile memory 914 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 916 may be implemented by flash memory and/or any other desired type of memory device. Access to the main memory 914, 916 is controlled by a memory controller. In the illustrated example, the volatile memory 914 is shown as storing the prediction report(s) 112 and the accuracy report(s) 114 of FIG. 1. The reports 112 and/or 114 may additionally or alternatively be stored on any other memory in or external from the processor platform 900.

The processor platform 900 of the illustrated example also includes an interface circuit 920. The interface circuit 920 may be implemented by any type of interface standard, such as an Ethernet interface, a universal serial bus (USB), and/or a PCI express interface.

In the illustrated example, one or more input devices 922 are connected to the interface circuit 920. The input device(s) 922 permit(s) a user to enter data and commands into the processor 912. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 924 are also connected to the interface circuit 920 of the illustrated example. The output devices 924 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 920 of the illustrated example, thus, typically includes a graphics driver card, a graphics driver chip or a graphics driver processor.

The interface circuit 920 of the illustrated example also includes a communication device such as a transmitter, a receiver, a transceiver, a modem and/or network interface card to facilitate exchange of data with external machines (e.g., computing devices of any kind) via a network 926 (e.g., an Ethernet connection, a digital subscriber line (DSL), a telephone line, coaxial cable, a cellular telephone system, etc.).

The processor platform 900 of the illustrated example also includes one or more mass storage devices 928 for storing software and/or data. Examples of such mass storage devices 928 include floppy disk drives, hard drive disks, compact disk drives, Blu-ray disk drives, RAID systems, and digital versatile disk (DVD) drives. In the illustrated example, the mass storage device 928 is shown storing the AMB 102 of FIG. 1. In other examples, the AMB 102 may be additionally or alternatively stored on any other memory in or external from the processor platform 900.

Coded instructions 932 used to implement the machine readable instructions of FIGS. 7 and/or 8 may be stored in the mass storage device 928, in the volatile memory 914, in the non-volatile memory 916, and/or on a removable tangible computer readable storage medium such as a CD or DVD.

From the foregoing, it will be appreciated that the above-disclosed methods, apparatus, and articles of manufacture improve capabilities of a processor platform to more accurately predict likelihoods or probabilities of injuries of players/participants in sporting events. For example, techniques disclosed herein include a cognitive framework that may be implemented on a processor platform to perform predictive analysis of performance data for sports players accessible from an associative database to predict the probability of injury of a target player on a target date. In some professional or collegiate sports leagues (e.g., basketball, baseball, American football, soccer/(international futbol), lacrosse, rugby, cricket, volleyball, swimming, tennis, track and field, etc.), the numbers of teams and players is so overwhelmingly large that it is difficult or impossible to meaningfully and usefully track and analyze player performance data to accurately predict injuries of players in a timely manner. For example, during a sport's season, games/competitions are so numerous and frequent that any attempt to analyze the voluminous amounts of player performance data to predict a player injury for any approaching game/competition date could take such an unpractically long time that the game/competition date would pass before arriving at such a player injury prediction. Examples disclosed herein employ processor platforms for performing predictive analysis of such voluminous amounts of player performance data to predict a probability of injury of a target player in a timely manner before a next target game/competition date. For example, techniques disclosed herein can be employed the day before or even the day of a target game/competition date to predict the probability of injury of the target player before the game/competition begins. In some examples, predictive analysis techniques disclosed herein may be used to determine a probability of injury of a target player within minutes or seconds. Due to the voluminous amounts of data needed to be analyzed to perform the predictive analyses disclosed herein, such fast predictive analyses would not be possible without using techniques disclosed herein to improve the data analysis and computation functions of a processor system. In some examples, techniques disclosed herein may be implemented using multi-core processor systems, multi-processor systems, and/or distributed processing to increases speeds of the predictive analyses.

Examples disclosed herein are better than prior solutions for a number of reasons. For example, the predictive analytics disclosed herein are based on performance and fitness records of similar players stored and updateable in real time in an associative memory database. As such, the predictive analyses disclosed herein are can be performed in real time on the most up-to-date player performance and fitness data. In addition, the predictive analyses disclosed herein are adaptive because they do not require any offline or prior training on annotated data, unlike prior methods based on traditional machine learning techniques. In addition, examples disclosed herein do not rely on a pre-learned model. Thus, the disclosed techniques are highly flexible in many respects including the ability to add or remove attributes (e.g., performance data parameters) or change similarity measuring parameters (e.g., performance data parameters on which similarity factors of the similar players are based).

Also, since examples disclosed herein are not based on traditional classification methods, they provide a comparatively much better performance under unbalanced or spare data. For example, the techniques disclosed herein provide a 70% true positive rate with just 1.6% positive samples in the data.

In addition, unlike model-based methods, techniques disclosed herein are not only based on injury data distributions of similar players, but also take into consideration injury histories of target players, which increases the accuracies of injury predictions. For example, techniques disclosed herein have been observed to achieve 80% prediction accuracy in predicting injuries for NBA players based on sports data (e.g., player performance data) provided by Kinduct Technologies.

Furthermore, examples disclosed herein leverage a rich sports database (e.g., an associative memory database) that is updated frequently with new data. As such, accuracies of predictions determined using examples disclosed herein improve over time, as more records are added, without any additional effort or human intervention, as there is no need to re-train or update the predictive analytics processes disclosed herein.

The following pertain to further examples disclosed herein.

Example 1 is a method to predict an injury for a target player on a target date. The method of Example 1 includes determining a first probability of injury of the target player based on probabilities of injuries of second players having similarities with the target player; determining a second probability of injury of the target player based on injuries of the target player; determining a third probability of injury of the target player based on the first probability of injury of the target player and the second probability of injury of the target player; and generating a report of a predicted probability of injury of the target player for the target date based on the third probability of injury of the target player.

In Example 2, the subject matter of Example 1 can optionally include that the first, second, and third probabilities of injuries of the target player are based on data collected between a start of a sport's season and the target date.

In Example 3, the subject matter any one of Examples 1-2 can optionally include that the second players are selected from an associative database, the second players having similarities with the target player by the target player being more similar to the second players than to third players in the associative database based on a priority ranking of performance data parameters.

In Example 4, the subject matter of any one of Examples 1-3 can optionally include that the performance data parameters include at least one of a physiological load, a mechanical load, a mechanical intensity, a physical intensity, a number of games played, average running seconds, average field goals, or previous injuries.

In Example 5, he subject matter of any one of Examples 1-4 can optionally include that determining the first probability of injury of the target player based on the probabilities of injuries of the second players is based on dividing (a) a sum of weighted probabilities of injuries for ones of the second players by (b) a sum of similarity factors of the second players.

In Example 6, the subject matter of any one of Examples 1-5 can optionally include that the probabilities of injuries for the ones of the second players are based on a number of games played and a number of injuries for each of the ones of the second players between a start of a sport's season and the target date.

In Example 7, the subject matter of any one of Examples 1-6 can optionally include that the sum of similarity factors is a sum of percentages representative of amounts of similarity between performance data parameters of the second players and the target player.

Example 8 is an apparatus to predict an injury for a target player on a target date. The apparatus of Example 8 includes a predictor and a report generator. The predictor is to: determine a first probability of injury of the target player based on probabilities of injuries of second players having similarities with the target player; determine a second probability of injury of the target player based on injuries of the target player; and determine a third probability of injury of the target player based on the first probability of injury of the target player and the second probability of injury of the target player. The report generator is to generate a report of a predicted probability of injury of the target player for the target date based on the third probability of injury of the target player.

In Example 9, the subject matter of Example 8 can optionally include that the first, second, and third probabilities of injuries of the target player are based on data collected between a start of a sport's season and the target date.

In Example 10, the subject matter of any one of Examples 8-9 can optionally include a data interface to query an associative database to select the second players in the associative database, the second players having similarities with the target player by the target player being more similar to the second players than to third players in the associative database based on a priority ranking of performance data parameters.

In Example 11, the subject matter of any one of Examples 8-10 can optionally include that the performance data parameters include at least one of a physiological load, a mechanical load, a mechanical intensity, a physical intensity, a number of games played, average running seconds, average field goals, or previous injuries.

In Example 12, the subject matter of any one of Examples 8-11 can optionally include that the predictor is to perform the determining of the first probability of injury of the target player based on the probabilities of injuries of the second players by dividing (a) a sum of weighted probabilities of injuries for ones of the second players by (b) a sum of similarity factors of the second players.

In Example 13, the subject matter of any one of Examples 8-12 can optionally include that the probabilities of injuries for the ones of the second players are based on a number of games played and a number of injuries for each of the ones of the second players between a start of a sport's season and the target date.

In Example 14, the subject matter of any one of Examples 8-13 can optionally include that the sum of similarity factors is a sum of percentages representative of amounts of similarity between performance data parameters of the second players and the target player.

Example 15 is tangible machine readable storage medium including instructions that, when executed, cause a processor to at least: determine a first probability of injury of the target player based on probabilities of injuries of second players having similarities with the target player; determine a second probability of injury of the target player based on injuries of the target player; determine a third probability of injury of the target player based on the first probability of injury of the target player and the second probability of injury of the target player; and generate a report of a predicted probability of injury of the target player for a target date based on the third probability of injury of the target player.

In Example 16, the subject matter of Example 15 can optionally include that the first, second, and third probabilities of injuries of the target player are based on data collected between a start of a sport's season and the target date.

In Example 17, the subject matter of any one of Examples 15-16 can optionally include that the instructions are to further cause the processor to query an associative database to select the second players, the second players having similarities with the target player by the target player being more similar to the second players than to third players in the associative database based on a priority ranking of performance data parameters.

In Example 18, the subject matter of any one of Examples 15-17 can optionally include that the performance data parameters include at least one of a physiological load, a mechanical load, a mechanical intensity, a physical intensity, a number of games played, average running seconds, average field goals, or previous injuries.

In Example 19, the subject matter of any one of Examples 15-18 can optionally include that determining the first probability of injury of the target player based on the probabilities of injuries of the second players is based on dividing (a) a sum of weighted probabilities of injuries for ones of the second players by (b) a sum of similarity factors of the second players.

In Example 20, the subject matter of any one of Examples 15-19 can optionally include that the probabilities of injuries for the ones of the second players are based on a number of games played and a number of injuries for each of the ones of the second players between a start of a sport's season and the target date.

In Example 21, the subject matter of any one of Examples 15-20 can optionally include that the sum of similarity factors is a sum of percentages representative of amounts of similarity between performance data parameters of the second players and the target player.

Example 22 is an apparatus to predict an injury for a target player on a target date. The apparatus of claim 22 includes: means for determining a first probability of injury of the target player based on probabilities of injuries of second players having similarities with the target player; means for determining a second probability of injury of the target player based on injuries of the target player; means for determining a third probability of injury of the target player based on the first probability of injury of the target player and the second probability of injury of the target player; and means for generating a report of a predicted probability of injury of the target player for the target date based on the third probability of injury of the target player.

In Example 23, the subject matter of Example 22 can optionally include that the first, second, and third probabilities of injuries of the target player are based on data collected between a start of a sport's season and the target date.

In Example 24, the subject matter of any one of Examples 22-23 can optionally include means for querying an associative database to select the second players in the associative database, the second players having similarities with the target player by the target player being more similar to the second players than to third players in the associative database based on a priority ranking of performance data parameters.

In Example 25, the subject matter of any one of Examples 22-24 can optionally include that the performance data parameters include at least one of a physiological load, a mechanical load, a mechanical intensity, a physical intensity, a number of games played, average running seconds, average field goals, or previous injuries.

In Example 26, the subject matter of any one of Examples 22-25 can optionally include that the first probability of injury of the target player is determined based on the probabilities of injuries of the second players by dividing (a) a sum of weighted probabilities of injuries for ones of the second players by (b) a sum of similarity factors of the second players.

In Example 27, the subject matter of any one of Examples 22-26 can optionally include that the probabilities of injuries for the ones of the second players are based on a number of games played and a number of injuries for each of the ones of the second players between a start of a sport's season and the target date.

In Example 28, the subject matter of any one of Examples 22-27 can optionally include that the sum of similarity factors is a sum of percentages representative of amounts of similarity between performance data parameters of the second players and the target player.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A method to predict an injury for a target player on a target date, the method comprising:
   accessing, by a query message, data stored in an associative database;
   determining, by executing an instruction with a processor, a first probability of injury of the target player based on probabilities of injuries of second players based on dividing (a) a sum of weighted probabilities of injuries for ones of the second players by (b) a sum of similarity factors of the second players, the second players selected based on a comparison of characteristics between the second players and the target player;
   determining, by executing an instruction with the processor, a second probability of injury of the target player based on injuries of the target player;
   determining, by executing an instruction with the processor, a third probability of injury of the target player based on the first probability of injury of the target player and the second probability of injury of the target player;

generating, by executing an instruction with the processor, a report of a predicted probability of injury of the target player for the target date based on the third probability of injury of the target player; and storing the report in computer memory.

2. The method as defined in claim 1, wherein the first, second, and third probabilities of injuries of the target player are based on data collected between a start of a sport's season and the target date.

3. The method as defined in claim 1, wherein the second players are selected from the associative database, the second players having similarities with the target player by the target player being more similar to the second players than to third players in the associative database based on a priority ranking of performance data parameters.

4. The method as defined in claim 3, wherein the performance data parameters include at least one of a physiological load, a mechanical load, a mechanical intensity, a physical intensity, a number of games played, average running seconds, average field goals, or previous injuries.

5. The method as defined in claim 1, wherein the weighted probabilities of injuries for the ones of the second players are based on a number of games played and a number of injuries for each of the ones of the second players between a start of a sports season and the target date.

6. The method as defined in claim 1, wherein the sum of similarity factors is a sum of percentages representative of amounts of similarity between performance data parameters of the second players and the target player.

7. An apparatus to predict an injury for a target player on a target date, the apparatus comprising:

a data interface to access, by a query message, data stored in an associative database;

a predictor to:
 determine a first probability of injury of the target player based on probabilities of injuries of second players by dividing (a) a sum of weighted probabilities of injuries for ones of the second players by (b) a sum of similarity factors of the second players, the second players selected based on a comparison of characteristics between the second players and the target player;
 determine a second probability of injury of the target player based on injuries of the target player; and
 determine a third probability of injury of the target player based on the first probability of injury of the target player and the second probability of injury of the target player;

a report generator to generate a report of a predicted probability of injury of the target player for the target date based on the third probability of injury of the target player; and computer memory to store the report.

8. The apparatus as defined in claim 7, wherein the first, second, and third probabilities of injuries of the target player are based on data collected between a start of a sport's season and the target date.

9. The apparatus as defined in claim 7, wherein the data interface is to query the associative database to select the second players in the associative database, the second players having similarities with the target player by the target player being more similar to the second players than to third players in the associative database based on a priority ranking of performance data parameters.

10. The apparatus as defined in claim 9, wherein the performance data parameters include at least one of a physiological load, a mechanical bad, a mechanical intensity, a physical intensity, a number of games played, average running seconds, average field goals, or previous injuries.

11. The apparatus as defined in claim 7, wherein the weighted probabilities of injuries for the ones of the second players are based on a number of games played and a number of injuries for each of the ones of the second players between a start of a sport's season and the target date.

12. The apparatus as defined in claim 7, wherein the sum of similarity factors is a sum of percentages representative of amounts of similarity between performance data parameters of the second players and the target player.

13. A tangible machine readable storage medium comprising instructions that, when executed, cause a processor to at least:

access, by a query message, data stored in an associative database;

determine a first probability of injury of a target player based on probabilities of injuries of second players based on dividing (a) a sum of weighted probabilities of injuries for ones of the second players by (b) a sum of similarity factors of the second players, the second players selected based on a comparison of characteristics between the second players and the target player;

determine a second probability of injury of the target player based on injuries of the target player;

determine a third probability of injury of the target player based on the first probability of injury of the target player and the second probability of injury of the target player;

generate a report of a predicted probability of injury of the target player for a target date based on the third probability of injury of the target player; and store the report in computer memory.

14. The tangible machine readable storage medium as defined in claim 13, wherein the first, second, and third probabilities of injuries of the target player are based on data collected between a start of a sport's season and the target date.

15. The tangible machine readable storage medium as defined in claim 13, wherein the instructions are to further cause the processor to query the associative database to select the second players, the second players having similarities with the target player by the target player being more similar to the second players than to third players in the associative database based on a priority ranking of performance data parameters.

16. The tangible machine readable storage medium as defined in claim 15, wherein the performance data parameters include at least one of a physiological load, a mechanical load, a mechanical intensity, a physical intensity, a number of games played, average running seconds, average field goals, or previous injuries.

17. The tangible machine readable storage medium as defined in claim 13, wherein the weighted probabilities of injuries for the ones of the second players are based on a number of games played and a number of injuries for each of the ones of the second players between a start of a sport's season and the target date.

18. The tangible machine readable storage medium as defined in claim 13, wherein the sum of similarity factors is a sum of percentages representative of amounts of similarity between performance data parameters of the second players and the target player.

19. An apparatus to predict an injury for a target player on a target date, the apparatus comprising:
- means for accessing, by a query message, data stored in an associative database;
- means for determining a first probability of injury of the target player based on probabilities of injuries of second players based on dividing (a) a sum of weighted probabilities of injuries for ones of the second players by (b) a sum of similarity factors of the second players, the second players selected based on a comparison of characteristics between the second players and the target player;
- means for determining a second probability of injury of the target player based on injuries of the target player;
- means for determining a third probability of injury of the target player based on the first probability of injury of the target player and the second probability of injury of the target player;
- means for generating a report of a predicted probability of injury of the target player for the target date based on the third probability of injury of the target player; and
- means for storing the report.

20. The apparatus as defined in claim 19, wherein the first, second, and third probabilities of injuries of the target player are based on data collected between a start of a sport's season and the target date.

21. The apparatus as defined in claim 19, further including means for querying an associative database to select the second players in the associative database, the second players having similarities with the target player by the target player being more similar to the second players than to third players in the associative database based on a priority ranking of performance data parameters.

22. The apparatus as defined in claim 21, wherein the performance data parameters include at least one of a physiological load, a mechanical bad, a mechanical intensity, a physical intensity, a number of games played, average running seconds, average field goals, or previous injuries.

* * * * *